United States Patent [19]

Arnold

[11] Patent Number: 5,576,197
[45] Date of Patent: Nov. 19, 1996

[54] POLYMERASE CHAIN REACTION CONTAINER AND METHODS OF USING THE SAME

[75] Inventor: Robert Arnold, San Diego, Calif.

[73] Assignee: Molecular Bio-Products, San Diego, Calif.

[21] Appl. No.: 418,537

[22] Filed: Apr. 7, 1995

[51] Int. Cl.$^6$ .............................. C12P 19/34; C12Q 1/68; C10G 73/36
[52] U.S. Cl. ................... 435/91.2; 435/6; 208/20; 208/21
[58] Field of Search .................. 435/6, 91.2; 208/20, 208/21

[56] References Cited

U.S. PATENT DOCUMENTS

| | | | |
|---|---|---|---|
| 4,617,261 | 10/1986 | Sheldon et al. | 435/6 |
| 4,705,866 | 11/1987 | Levenson et al. | 560/159 |
| 4,751,313 | 6/1988 | Levenson et al. | 548/304.1 |
| 4,754,065 | 6/1988 | Levenson et al. | 562/564 |
| 4,803,297 | 2/1989 | Levenson et al. | 560/159 |
| 4,882,731 | 4/1989 | Watson et al. | 435/6 |
| 5,047,519 | 9/1991 | Hobbs et al. | 536/27.14 |
| 5,106,729 | 4/1992 | Lindsay et al. | 435/6 |
| 5,151,507 | 9/1992 | Hobbs et al. | 536/27.2 |
| 5,168,063 | 12/1992 | Doyle et al. | 435/240.27 |
| 5,225,546 | 7/1993 | Dryja et al. | 435/6 |
| 5,262,529 | 11/1993 | Dryja et al. | 435/6 |
| 5,266,317 | 11/1993 | Tomalski et al. | 435/69.1 |
| 5,266,689 | 11/1993 | Chakraborty et al. | 435/6 |
| 5,278,298 | 1/1994 | Chakraborty et al. | 435/6 |
| 5,282,543 | 2/1994 | Picozza et al. | 435/287 |
| 5,284,940 | 2/1994 | Lin et al. | 435/6 |
| 5,288,845 | 2/1994 | Chakraborty et al. | 435/6 |
| 5,298,613 | 3/1994 | Chakraborty et al. | 435/6 |
| 5,304,473 | 4/1994 | Belagaje et al. | 435/69.7 |
| 5,314,813 | 5/1994 | Peterson et al. | 435/172.3 |
| 5,320,840 | 6/1994 | Camble et al. | 424/85.1 |
| 5,324,630 | 6/1994 | LeFebvre et al. | 435/6 |
| 5,332,672 | 7/1994 | Conover et al. | 435/69.1 |
| 5,349,123 | 9/1994 | Shewmaker et al. | 435/69.1 |
| 5,349,125 | 9/1994 | Holton et al. | 536/23.6 |
| 5,349,126 | 9/1994 | Chappell et al. | 435/69.1 |
| 5,359,050 | 10/1994 | Chakraborty et al. | 435/6 |
| 5,364,591 | 11/1994 | Green et al. | 435/6 |
| 5,370,996 | 12/1994 | Metz et al. | 435/69.1 |
| 5,411,876 | 5/1995 | Bloch et al. | 435/91.2 |
| 5,413,924 | 5/1995 | Kosak et al. | 435/177 |

FOREIGN PATENT DOCUMENTS

| | | | |
|---|---|---|---|
| 572057 | 1/1993 | European Pat. Off. | |
| WO91/12342 | 8/1991 | WIPO | C12Q 1/68 |

OTHER PUBLICATIONS

Biotechniques Aug. 1994. Hotstart PCR Ad. In Biotech. Aug. 1994.

Biotech Equipment Update, (Sep. 1994), "Hotstart 100 storage and reaction tubes for advanced PCR applications offered", 2(9):DIALOG #02480358.

Hebert et al, (1993), "Increased PCR sensitivity by using paraffin wax as a reaction mix overlay", Mol. Cell. Probes 7:249–252.

Kemp et al, (1990), "Simplified colorimetric analysis of polymerase chain reactions: detection of HIV sequences in AIDS patients", Gene 94:223–228.

(List continued on next page.)

Primary Examiner—Stephanie W. Zitomer
Assistant Examiner—Jeffrey Fredman
Attorney, Agent, or Firm—Campbell & Flores LLP

[57] ABSTRACT

The invention describes a polymerase chain reaction container and methods of using the same that greatly simplify and improve the polymerase chain reaction. Specifically, the invention describes a PCR container comprising a container suitable for PCR with wax attached to the inside surface of the container. The wax is positioned at or above an estimated meniscus position of a PCR mixture. The wax melts at PCR temperatures and covers the surface of the PCR mixture thereby prevents evaporation during thermal cycling. The invention is superior to current methods, in part, because it reduces preparation time, potential sources of contamination and adverse effects on PCR.

10 Claims, 5 Drawing Sheets

OTHER PUBLICATIONS

Dale, (1992), "Direct microtiter plate sequencing of PCR–amplified M13 clones from plaques using dried reagents", Biotechniques 12(2:)194, 196–197.

Cooke, (1992), "Inexpensive was for PCR protocols", Trends Genet. 8(9):301.

Blair et al, (1994), "Wax–embedded PCR reagents", PCR Meth. Appl. 4(3):191–194.

Sparkman, (1992), "Paraffin wax as a vapor barrier for the PCR", PCR Meth. Appl. 2(2):180–181.

Tilston, P and Corbitt G. "Detection of Hepatitis C Virus RNA in Serum, by Combining Reverse Transcription and Polymerase Chain Reaction in One Tube." J. Virol. Meth. 44:57–66 (1993).

Kaijalainen, S. et al. "An Alternative Hot Start Technique for PCR in Small Volumes Using Beads of Wax–embedded Reaction Components Dried in Trehalose." Nucleic Acids Res. 21:2959–2960 (1993).

Horton, Robert M. et al., "AmpliGrease: Hot Start PCR Using Petroleum Jelly." Biotech., 16:42–43 (1994).

Nuovo, Gerard J. et al., "Importance of Different Variables for Enhancing In Situ Detection of PCR–amplified DNA." PCR Methods and Applications. 2:305–312 (1993).

Lin, Hsiang Ju et al., "Polymerase Chain Reaction Assay for Hepatitis C Virus RNA Using a Single Tube for Reverse Transcription and Serial Rounds of Amplification with Nested Primer Pairs." J., Medical Vir. 38:220–225 (1992).

Wainwright and Seifert, "Paraffin Beads Can Replace Mineral Oil as an Evaporation Barrier in PCR." BioTech. 14:35–36 (1993).

POLYMERASE CHAIN REACTION CONTAINER AND METHODS OF USING THE SAME

This invention describes polymerase chain reaction containers and methods that greatly simplify and improve the polymerase chain reaction. The polymerase chain reaction has broad application in the fields of genetics, molecular biology, cellular biology, analytical chemistry, clinical chemistry, agriculture, anthropology, and forensic science.

BACKGROUND OF THE INVENTION

The polymerase chain reaction (PCR) is utilized for the exponential amplification of one or more specific nucleic acid(s) of interest (herein "target"), particularly deoxyribonucleic acid (DNA) target(s). By utilizing primer sets which identify a particular nucleic acid sequence, a thermostable DNA polymerase (herein "polymerase"), and optimal temperature cycling, millions of copies of a nucleic acid sequence can be made from limited starting amounts. In theory, the method can amplify a single nucleic acid molecule although, in practice, more than one molecule may be required. Moreover, the PCR method generally has excellent fidelity in reproducing nucleic acid molecules identical to the target.

In the simplest terms, the polymerase faithfully produces a nucleic acid sequence that is the complement to the target. The polymerase requires that a primer bind to the target in order for the polymerase to synthesize the complement. In the case of DNA, the target and its complement form a double strand target-complement molecule. For the polymerase to produce more targets, the double strand target-complement molecule must be separated into the two single-strand molecules.

The PCR is thermally cycled to repetitively separate and form double strand target-complement molecules. Usually, the PCR is thermally cycled in a prescribed program involving three temperatures. The first temperature, approximately 94° C., denatures the nucleic acid from the double strand form into the single strand form. The second temperature, typically about low 60° C., anneals the primer to the single strand target. The third temperature, about 72° C., allows the polymerase reaction to elongate the primers and the two strands anneal to form double strand nucleic acid. The cycle is repeated until a sufficient number of nucleic acid copies have been made. When a double stranded target is amplified, each thermal cycle amplifies the target by about $2^n$, where n is the number of thermal cycles completed.

PCR has various competitive side reactions that occur at relatively low temperature, generally below 60° C. Competitive side reactions include, for example, mis-priming, the binding of primers to the wrong target sequence and primer dimers, the binding together of two primers. The competitive side reactions create sequences other than the target that are amplified. To counteract these reactions, a modified PCR method has been developed (herein "hot start") in which at least one key reagent, such as the polymerase or target, is withheld from the PCR mixture until the PCR mixture is heated, usually to the annealing temperature. Because the PCR cannot begin until the key reagent is added and PCR begins at the optimum temperature, the competitive side reactions are significantly reduced.

Regardless of the PCR method used, evaporation from the PCR mixture during thermal cycling must be prevented. Typically, a hydrophobic material, such as mineral oil, is layered onto the PCR reaction mixture to prevent evaporation during thermal cycling. The hydrophobic materials floats on the PCR mixture because it not miscible with and has a lower density than the PCR mixture. By completely covering the surface, the hydrophobic material seals and prevents water evaporation from the PCR mixture. A variant method is to add a small solid wax ball that melts at PCR temperatures and the melted wax covers the surface of the PCR mixture. A commercially available wax ball used for this purpose is AMPLIWAX available from PERKIN-ELMER, Norwalk, Conn., U.S.A.

A major problem with hydrophobic layering methods is the possibility of contamination. Typically, a technician loads the hydrophobic material and the technician himself is a significant potential source nucleic acid contamination. Any procedure in which a technician handles the PCR container has the potential to contaminate the sample. Precautions can be taken to reduce this risk, such as wearing gloves, but they do not guarantee contamination prevention. Methods that eliminate technician loading of the hydrophobic material are desirable because such methods significantly reduce the potential for contamination.

The current hydrophobic layering methods can also cross-contaminate target among PCRs. For example, the device used to load the hydrophobic material, such as a pipet or tweezers, can become contaminated by target and, if the same device is used repetitively, cross-contaminate other PCRs. The source of hydrophobic material, such as wax balls, can become contaminated by an amplifiable material that source will cross-contaminate other PCRs. Improper loading of the hydrophobic material can cause target to splatter out of the container and cross-contaminate other PCRs. Methods that eliminate loading the hydrophobic material are desirable because such methods significantly reduce the potential for cross-contamination by target.

Another disadvantage to current hydrophobic layering methods is that they are tedious and time-consuming. Typically, a technician carefully pipets oil, layers grease or adds a wax ball onto the surface of each PCR mixture in each individual container. This task becomes tedious to perform when a large number of PCRs are processed. More important, loading the hydrophobic material, whether manually or by automated means, takes a significant amount of time to perform when a large number of PCRs are run. A method that eliminates loading the hydrophobic material on each PCR mixture is desirable because it would significantly reduce the amount of time it takes to prepare a large number of PCRs.

Another method used to prevent evaporation is to use a microtube containing solid wax at the bottom of the tube. In this method, the PCR mixture is added on top of the solid wax at the bottom of the microtube. The wax and PCR mixture must be phase inverted by centrifugation, so that wax covers the surface of the PCR mixture when melted.

Although the current microtube containing wax method avoids many of the disadvantages of the hydrophobic layering methods, the phase inversion step is a severe limitation to this method. The phase inversion can be incomplete with PCR mixture remaining above the wax and subject to water evaporation which adversely effects the amplification reaction. Forcing the phases through each other can result in adsorption of PCR mixture in the wax. The water trapped in the wax can react violently when heated and spatter droplets of PCR mixture with obvious adverse effects on amplification. Forcing phase inversion can cause reagents in the PCR mixture to absorb onto the wax and effectively remove the reagents from the PCR. A microtube containing wax method that does not require phase inversion is desirable to reduce incomplete phase separation, splattering and reagent absorption.

Another disadvantage to the current microtube containing wax method is that the centrifugation takes time and limits sample through-put. For large numbers of samples, the centrifugation step adds a significant amount of preparation time. A microtube containing wax method that does not require a centrifugation step is desirable to reduce preparation time.

There thus exists a need for a method that prevents water evaporation during PCR without the contamination concerns and time-consuming preparation steps of current hydrophobic layering methods. Further, a method is needed that prevents water evaporation without requiring phase inversion of wax and PCR mixture. The present invention satisfies these needs and provides related advantages as well.

SUMMARY OF THE INVENTION

The present invention provides a PCR container comprising the following elements: a container wherein the container is suitable for PCR and the container has a closed end, an open end distal to the closed end and a lumen; and wax attached to the inside surface of the container at a position that is at about or above the meniscus of an aqueous PCR mixture; the wax does not completely occlude the lumen of the container; the wax is solid at or below about 40° C. and liquid at or above PCR temperatures; the wax, when liquified, spontaneously covers the surface of a PCR mixture; and the wax is in an amount that, when liquified, completely covers the surface of the PCR mixture in the container. Embodiments of the PCR container include, for example, microtubes and wells in a microtiter plate.

In another aspect, methods of PCR are provided that have fewer steps than current methods and thereby offer significant advantages.

DETAILED DESCRIPTION OF THE INVENTION

Figure 1:
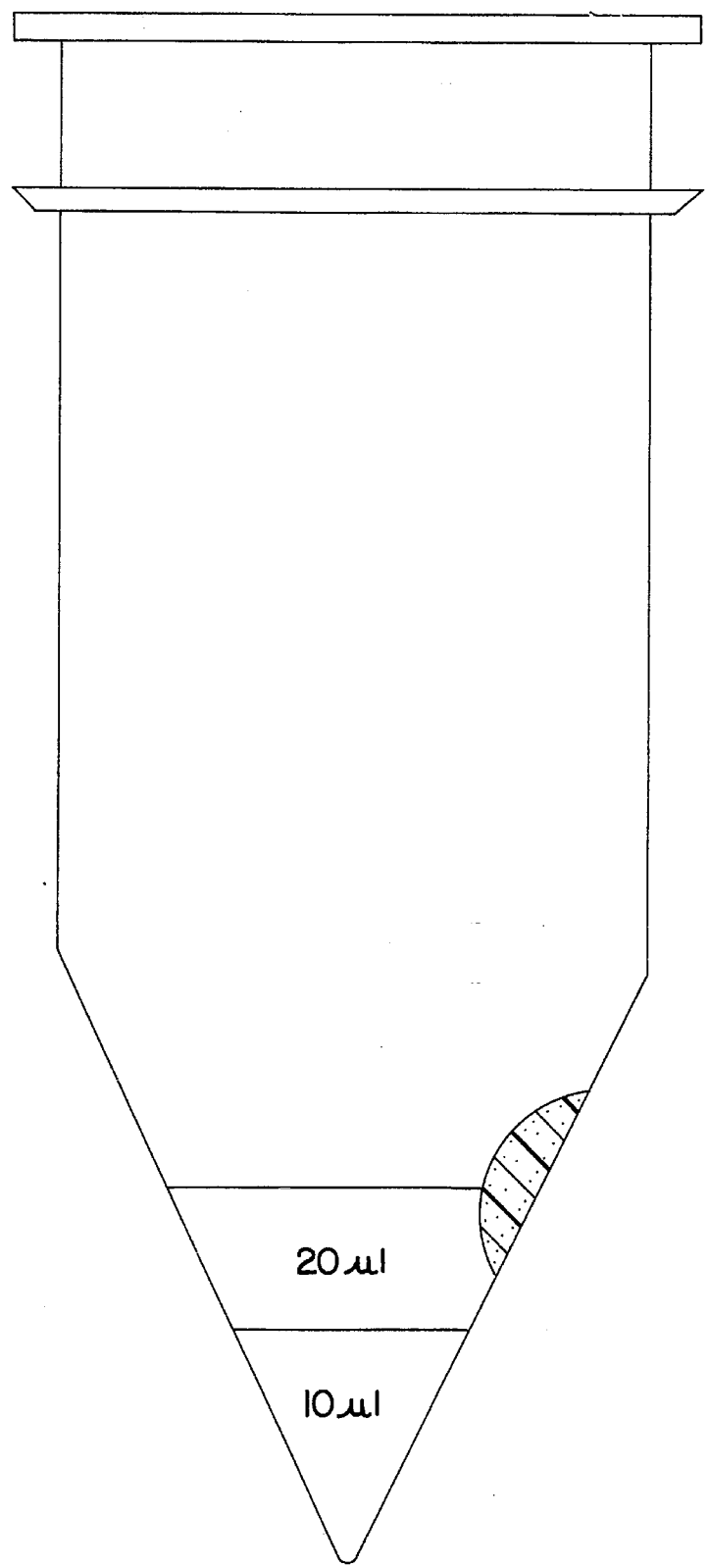
FIG. 1 is a cross-sectional view of a PCR microtube according to the teaching of the present invention. This figure shows a 0.2 ml microtube and attached solid wax. The wax is attached to the inside surface of the microtube at a position at about or above the expected meniscus position of a PCR mixture. The relationship between the wax position and the meniscus of two volumes of PCR mixture, 10 µl and 20 µl, are shown. The minimum amount of wax for this tube size is about 0.015 g. This figure shows the wax as it is prior to PCR heating.
Figure 2:
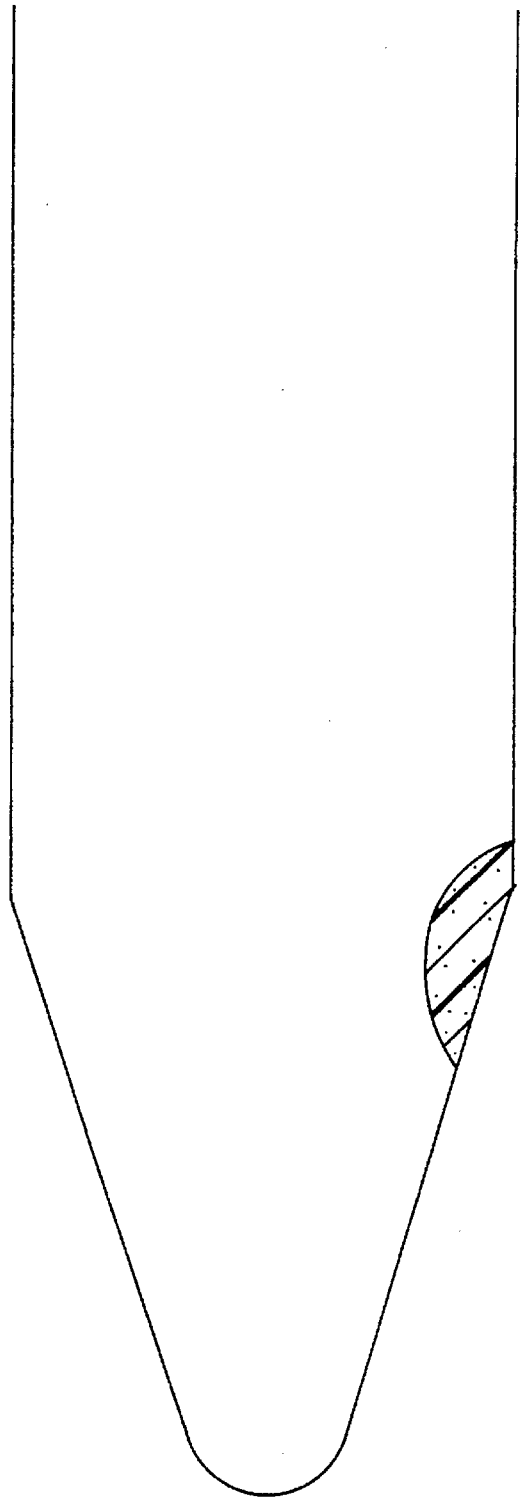
FIG. 2 is a cross-sectional view of a PCR microtube according to the teaching of the present invention. This figure shows a 0.5 ml microtube and attached solid wax. The wax is attached to the inside surface of the microtube at a position at about or above the expected meniscus position of a PCR mixture. The figure shows the approximate position of the wax above the closed end of the tube.

The invention is a PCR container with wax attached to the inside surface at a strategic position such that the wax, when melted, covers the surface of a PCR mixture added to the container and prevents water evaporation during PCR thermal cycling. The wax is positioned at or above an estimated meniscus position of a PCR mixture added to the container. The wax does not completely occlude the lumen of the container so that PCR mixture can be added to the container.

The wax attached to the container is solid at or below about 40° C. but melts and becomes liquid when heated to PCR temperatures. Heating the wax causes the wax to float over and cover the surface of the PCR mixture. The liquid wax spontaneously covers the surface upon heating because of the immiscibility of wax and water. The strategic position of the wax results in a wax layer on top of the PCR mixture, the phase orientation required to seal the PCR mixture from evaporation. If the container is cooled to below 40° C. after the wax is melted, the wax solidifies over the surface of and seals the PCR mixture in the container.

A major advantage of positioning the wax at or above the PCR mixture meniscus is that wax and PCR mixture are in the correct orientation to prevent water evaporation. In the current microtube containing wax method, the wax is initially below the PCR mixture and the wax and PCR mixture must be inverted by centrifugation. Using the invention, there is no need to centrifuge the container to invert the wax and PCR mixture because the wax and PCR mixture are in the proper orientation. All that one need do is add the PCR mixture to the container. As a result, the invention makes PCR significantly easier to perform and has a shorter preparation time than the current microtube containing wax method. Reducing sample preparation time is particularly advantageous for conducting a large number of PCRs.

Another advantage of avoiding the wax-PCR mixture phase inversion step of the current microtube containing wax method is that the conditions for amplification are improved. Heating the invention to PCR temperatures causes the wax to gently flow over and cover the surface of the PCR mixture. The sealing process thus occurs without disturbing the PCR mixture. In contrast, the current microtube containing wax method requires forcing the wax through the PCR mixture. This process can have deleterious effects on amplification, such as incomplete phase inversion, splattering and reagent extraction. Thus, the invention seals the surface of the PCR mixture without the deleterious effects on amplification that can result from centrifugation using the current method.

The invention also has substantial advantages over the current hydrophobic layering methods. Since the wax is preloaded in the PCR container, the invention eliminates the loading oil, grease or wax ball to the container. As discussed above, elimination of this step significantly reduces potential sources of contamination. For example, a technician does not load a wax ball and therefore a significant potential source of contamination is removed from the procedure. Moreover, because the wax is preloaded into individual PCR containers, the invention cannot cross-contaminate target among PCRs as can occur in current hydrophobic sealing methods.

Further, since the wax is preloaded in the container, all one need do to prepare for PCR is add the PCR mixture. In contrast, hydrophobic layering methods require that the oil, grease or wax ball be added to each PCR container, a time consuming process when a large number of PCR are conducted. The invention thus has a substantially shorter PCR preparation time than current methods.

The containers of the invention can be made by any means that deposits an appropriate amount of wax at the appropriate position on the inside surface of the PCR container. For example, a heated nozzle having a lumen that allows liquid wax to pass through a nozzle from a reservoir of liquid wax to the desired location in the container can be used. The nozzle can be any dimension so long as it fits into the lumen of the container and can be made of any material suitable for heating wax, such as, metal, for example, aluminum or stainless steel. The liquid wax can be placed at the appropriate position within the PCR container by adjusting the relative position of the nozzle to the container. For example, a wheel attached to the nozzle by a set screw or machine threaded advance mechanism can be used to adjust the relative position of the nozzle to the container. The wax and nozzle can be heated using any device that achieves and maintains a temperature resulting in liquid wax having suitable flow characteristics for deposition. For example, a heating device can be an electrical resistance heater with an adjustable temperature regulator. The wax can be dispensed using any device that allows precise control of the amount of wax. For example, a valve can be opened for a period of time to allow a precise amount of liquid wax to flow to the container. The liquid wax flow through the nozzle can be caused by any means capable of doing so including, for example, pressurized gas. The amount of wax deposited can be assayed by weight.

The invention is also directed to a PCR method having fewer steps to perform than current methods. PCR methods are well known in the art and described in many references, including, for example, the above-cited references. Currently, a PCR mixture is added to a container, sealed to prevent evaporation and thermally cycled. After completion of the thermal cycle, the target is separated and purified using well known methods. The method of the invention simplifies the current method by eliminating the sealing step of current PCR methods. For example, there is no need to load a solid wax ball or centrifuge the microtube. As described above, elimination of sealing steps provides substantial advantages over current methods.

Further, the invention is directed to a hot start PCR method that has fewer steps than current hot start methods. Hot start is a well known PCR method for reducing unwanted PCR by-products. Standard hot start PCR methods are described in many references, including, for example, the above-cited references. In hot start PCR, a PCR mixture lacking a critical reagent(s) is heated to the polymerase chain reaction temperature and, at that temperature, the missing critical reagent(s) is added to the PCR mixture. Usually, the missing critical reagent is the thermostable DNA polymerase. The target is separated and purified using well known methods. As above, the invention simplifies the hot start PCR method by eliminating the sealing step of prior art methods, such as loading the solid wax ball or centrifuging the microtube. As described above, the elimination of sealing steps provides substantial advantages over current methods.

Figure 5:
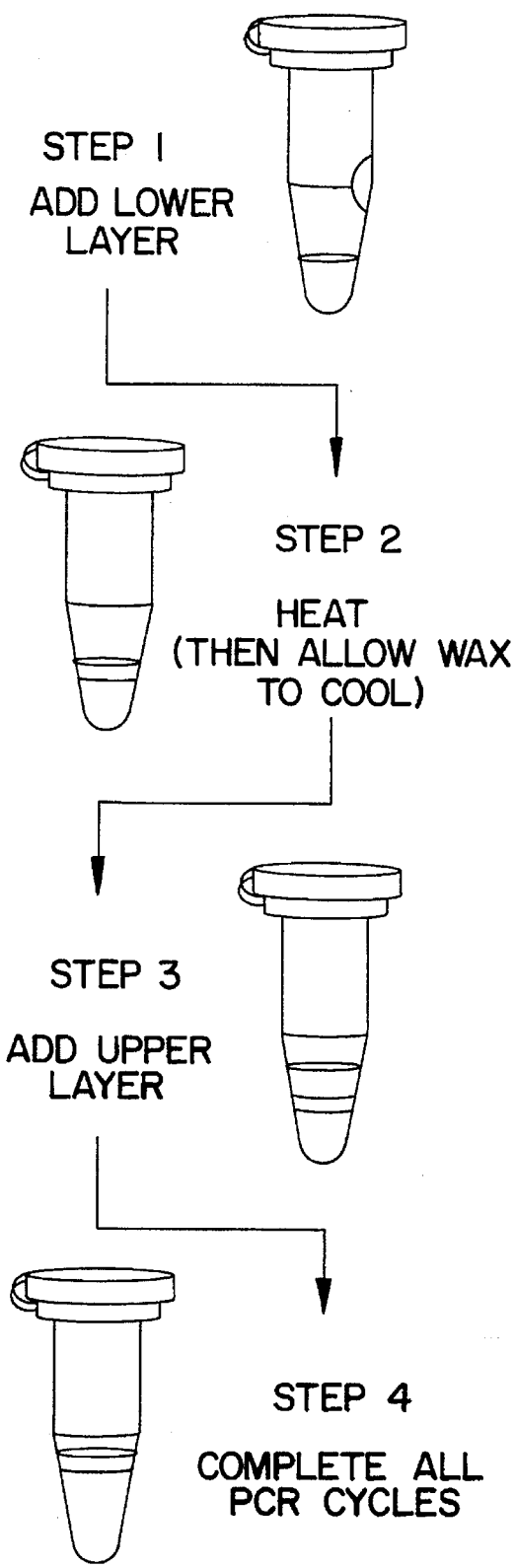
FIG. 5 is diagram of the hot start method using the claimed invention.

A hot start method of the claimed invention is diagramed in FIG. 5. For example, a first solution containing primers, buffers, and dNTPs in water is added to the containers of the instant invention. The container is heated to approximately 90° C. to melt the wax and cover the first solution. The container is cooled to room temperature to solidify the wax and seal the first solution. If desired, the sealed tube can be stored at low temperature, for example −20° C., for months. A second layer containing target, buffer and polymerase in water is added is placed in the container on the wax barrier above the first solution. The container is heated to the denaturation temperature and the wax barrier melts and floats to the surface of the solution. The first and second solutions mix together to form a PCR mixture and the container is thermally cycled to amplify the target. After the thermal cycling is complete, a pipet is used to penetrate the wax barrier and remove the PCR mixture.

In the hot start method of the claimed invention, the wax barrier between the first and second solution spontaneously floats to the surface of the solution. The first solution below the wax barrier allows the wax barrier to spontaneously float to the surface. In contrast, current containers having wax is at the bottom of the microtube lack the aqueous solution below the wax. As a result, the wax in these containers does not spontaneously float to the surface of a solution added above the wax.

The term "wax" as used herein is any hydrophobic material compatible with PCR and not miscible in water that is a solid at or below about 40° C. and a liquid at about PCR temperatures. The term "PCR temperatures" as used herein is the temperature at which PCR is conducted and includes the denaturation temperature, about 80° to 105° C., and the annealing and elongation temperatures at about 40° to 75° C. Wax known for use in PCR is preferable. A preferred wax is one having a low microcrystalline content. Typical useful waxes include paraffin, PARAPLAST, ULTRAFLEX, and BESQUARE 175. A particularly useful wax is CERESINE 130/135 (LCM 130/135) manufactured by KOSTER KEUNEN INC. Waxes can be prepared by mixing waxes with one another or other substances in any ratios that achieve the required characteristics. Wax is sterilized before use using any method known effective for this purpose. For example, the wax can be heated and filtered prior to use.

The amount of wax is that amount sufficient to cover the surface of the PCR mixture after melting. The amount can be determined by routine experimentation. The amount varies depending on several parameters, including, for example, the size of the container and the type of PCR desired. For example, amounts ranging from 0.010 to 0.04 g per PCR container are useful and, more specifically, 0.015 to 0.020 g or 0.025 g wax in a 0.2 ml microtube and 0.023 to 0.029 g or 0.04 g wax in a 0.5 ml microtube are useful. If it is necessary to pipet through the wax surface, the minimum amount of wax covering the PCR mixture is desirable to allow easy penetration of the pipet through the wax.

The position of the wax within the PCR container is critical. The wax must be positioned such that it spontaneously floats on and covers the PCR mixture surface when melted. As discussed above, wax below the PCR mixture does not spontaneously float on the surface. The wax must be positioned about at or above the meniscus of the PCR mixture. The wax must be positioned such that the wax will melt when the container is heated to PCR temperatures. For example, wax at or above about the meniscus and proximal to the heating device is useful. If a heating bock is used to heat the container, wax positioned at or above the meniscus and below the upper surface of the heating block is preferred.

Although the position varies depending on the dimensions of the PCR container, the volume of PCR mixture and the amount of wax, the appropriate position can be easily determined by routine experimentation. For example, wax positioned not less than 0.1 or more than 0.6 inches from the closed end of a container is useful. For a 0.5 ml conical microtube and 40 µl PCR mixture, the wax is positioned not less than 0.196 inches or greater than 0.591 inches from the closed end. More preferably, the wax is positioned between 0.25 and 0.55 inches from the closed end of a 0.5 ml conical microtube containing 40 µl PCR mixture. For a 0.2 ml conical microtube containing 20 µl PCR mixture, the wax is positioned not less than 0.118 inches or greater than 0.512 inches from the closed end. More preferably, the midpoint of the wax is positioned at 0.170 inches from the closed end of a 0.2 ml conical microtube containing 20 µl PCR mixture.

The wax can be distributed on the inside surface of the PCR container in any manner that allows the wax to spontaneously cover the PCR mixture surface when melted. Suitable wax distributions on the inside surface of the PCR container include a single bead, several beads or an annulus.

The term "container" or "PCR container" as used herein is an object having a closed end, an open end distal to the closed end and forming a lumen that is compatible with PCR and wax attachment. The defining features of a container compatible with PCR are that the container is made of a material which does not inhibit PCR, that can withstand temperatures in the range of about 20° to 100° C. while retaining substantially the same size and shape, and that can, together with the PCR mixture and wax, be capable of completing 40° C. temperature changes in the 50° to 100° C. range in an interval of not more than about four minutes. The defining feature of wax attachment is that the wax, when solidified on the container, remains attached to the container during routine shipping and handling. The container can have a tightly fitting lid. The container can have shapes which fit tightly in a well(s) of a machined metal heating block of commercially available thermal cyclers.

Examples of a PCR container include a microtube, microtiter plate and microscope slide containers. Microtubes for PCR are preferred. Containers appropriate for holding 20 to 200 µl of PCR mixture are useful. Commonly used containers capable of holding about 0.1 to 0.7 ml are suited for PCR. Container holding about 0.2, 0.5 and 0.6 ml are particularly well suited. Containers suitable for PCR are commonly molded from polypropylene although other materials can be used. An example of microtubes are those having a conical bottom half and a cylindrical top half. Suitable microtubes are available from EPPENDORF, QUALITY SCIENTIFIC PLASTICS, ROBBINS SCIENTIFIC, and PERKIN-ELMER. A microtiter plate is simply a group of wells in an ordered array on a plate.

A microscope slide container is different from the microtube and microtiter plate. This container is used to conduct PCR on a tissue section or cells attached to a microscopic slide. In this system, cone or ring structures are attached to the microscopic slide to form a PCR container. The PCR mixture added to the PCR container formed on the microscopic slide. The wax can be attached to the inside surface of the cone or ring. Microscope slide containers are available from GENE CLONE.

The term "PCR mixture" and "aqueous PCR mixture" refers to all the reagents required and used for PCR. The reagents and their amounts are well known in the art and described in various sources including, for example, the above-cited references. Briefly, the PCR mixture includes: one or more target(s); a thermostable polymerase, such as *Thermus aquaticus* polymerase I (Taq); at least four nucleoside triphosphates, for example dATP, dTTP, dCTP, and dGTP; oligonucleotide primer(s), usually two are needed defining a sequence complementary to the two ends of the target to be amplified; a magnesium compound, for example $MgCl_2$, appropriate salts, such as KCl, and an appropriate volume of water that is appropriately buffered, such as pH 8–9. Oligonucleotide primers includes nested primers that are designed to enhance amplification of a target following an initial amplification. Nested primers are complementary to sequences in the target that are different from the primers in the initial amplification. Small volumes of PCR mixture are used in the invention. Typically, 10 to 200 µl of total reaction volume are used.

Thermal cycling refers to changing the temperature of the PCR mixture between the polymerase reaction temperature and the separation temperature. There are many well known methods for thermal cycling known in the art, including, for example those in the references cited above. Perhaps the simplest method of thermal cycling is to manually move the PCR containers between devices having denaturation temperature and annealing and elongation temperatures, such as hot water baths, hot metal blocks, ovens and microwave ovens. More sophisticated methods include using a thermal cycler, an automated device for controlling the PCR reaction temperature and rates of temperature change within the limits required for the PCR. An example of a thermal cycler is that commercially available from PERKIN ELMER. Normally the temperature limits are about 40° to 105° C.

The claimed containers can also be used to for other applications. For example, the claimed containers can be used to store aqueous samples, particularly aqueous samples containing DNA, by heating the container to a temperature that melts the wax and cooling the container to a temperature that solidifies the wax. The claimed container can be used for reverse transcription PCR in one tube. The reverse transcription reagents are placed in the container, the container heated to a temperature that melts the wax and PCR mixture added on top of the wax barrier. Further, the claimed container can be used for post PCR reactions, such as transcription and translation. The transcriptional and translational reagents are loaded on top of the wax barrier after PCR is completed.

PCR methods and apparatus are generally known to those skilled in the art. Methods and apparatus disclosed in U.S. Pat. Nos. 4,683,195, 4,683,202 and 4,965,188, WO 91/12342, Mullis, K. B., F. Ferre and R. A. Gibbs, *The Polymerase Chain Reaction*, Birkhauser, Pub., Boston (1994), Hansen, H. and Hilmar, L., "Automated 'Hot Start' PCR Using Mineral Oil and Paraffin Wax," *BioTechniques* 14(1):31–32 (1993), Horton, R. M. et al., "AmpliGrease: 'Hot Start' PCR Using Petroleum Jelly," *BioTechniques* 16(1):42–44 (1994), Nuovo, G. J. et al., "Importance of Different Variables for Enhancing In Situ Detection of PCR-amplified DNA" in *PCR Methods and Applications*, Cold Spring Harbor Laboratory Press, pp. 305–312 (1993), Lin et al., "Polymerase Chain Reaction Assay for Hepatitis C Virus Using a Single Tube for Reverse Transcription and Serial Rounds of Amplification with Nested Primer Pairs," *J. Med. Virol.* 38:220–225 (1992) and Wainwright L. A. and H. S. Seifert, "Paraffin Beads Can Replace Mineral Oil as an Evaporative Barrier in PCR," BioTechniques 14(1):35–36

(1993) and Tilston, P. and G. Corbitt, "Detection of Hepatitis C virus RNA in Serum, by Combining Reverse Transcription and Polymerase Chain Reaction in One Tube," *J. Virol Methods* 44:57–66 (1993) are incorporated herein by reference.

The following example is intended to illustrate but not limit the present invention.

EXAMPLE I

A suitable microtube for hot start PCR contains about 0.023 to 0.037 g of wax placed between 0.25 and 0.55 inches from the bottom of a 0.5 ml microtube. Another suitable microtube for hot start PCR contains about 0.015 to 0.05 g of wax placed approximately 0.15 inches from the bottom of a 0.2 ml microtube. Microtubes containing wax can be made using the following equipment and procedures.

Microtubes containing wax are made in an environment that minimizes contamination. Precautions taken include equipping personnel with sterile latex gloves, hair bouffant, face mask, lab coat and shoe covers. All work is done under a Class 100 laminar flow hood. Personnel must follow good hygiene and housekeeping procedures in particular gloves must be changed immediately after contacting hair, skin or clothing. All surfaces and equipment are cleaned with solutions which remove nucleic acid and nuclease activity such as RNase AWAY from MOLECULAR BIO-PRODUCTS. Germicidal ultraviolet lights irradiate the work area when personnel are not present.

CERESINE 130/135 wax from KOSTER KEUNEN INC. is sterilized by heating to about 100° C. for about 60 minutes and filtering through a sterilizing filter. Sterilizing filters used is a NALGENE BOTTLE TOP FILTER having a cellulose acetate membrane and 0.2 µ meter diameter pore size. The filtered wax is stored at room temperature in the storage bottle used to capture the filtrate.

Figure 3A:
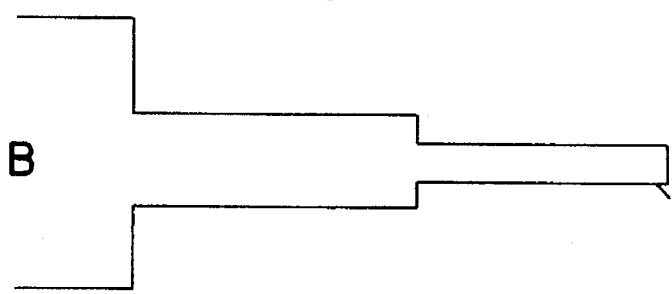
FIGS. 3A, B and C is a projection diagram of nozzles used to apply the wax to the side of the tube. Two nozzles having different dimensions are shown. Each nozzle contains a lumen through which liquid wax can pass. The liquid wax comes out of the nozzle tip, labeled structure A, and is deposited on the inside container wall. The wax and nozzle are heated and the wax dispensed by a wax heating and dispensing device, labeled structure B.
Figure 3B:
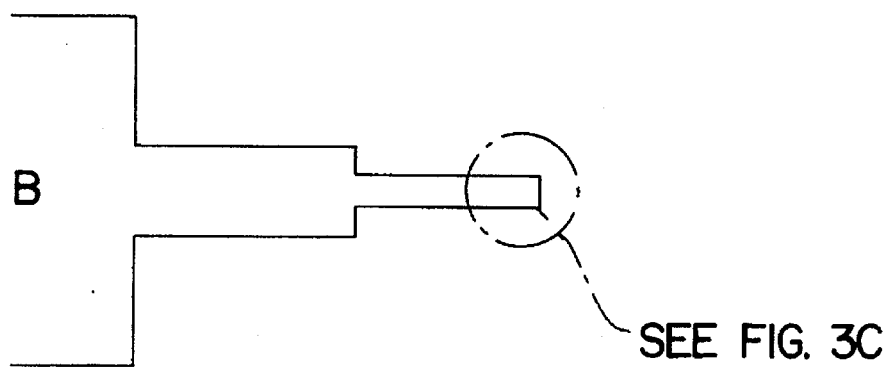
Figure 3C:
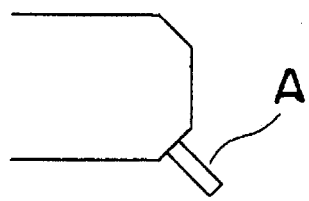

The nozzle shown in FIGS. 3A, B and C contains a lumen through which liquid wax can pass. The nozzle is connected to a TRIDAK Model 510 wax heating system that contains a 20 oz heated aluminum reservoir and a controller that adjusts the reservoir and nozzle temperatures so as to obtain optimal liquid wax viscosity characteristics. The reservoir temperature is 93° C. and the nozzle temperature is 89° C.

The TRIDAK Model 510 and TRIDAK Model 775 heated precision dispensing valve are used to control the amount of wax dispensed. The dispensing system contains a valve which allows liquid wax to flow for a precise and adjustable amount of time. The system contains a snuff-back capability that prevents dripping and eliminates nozzle air entrapment. A pressurized air supply powers the dispensing system and a foot switch activates the dispensing valve.

The amount of wax dispensed is determined by several parameters, such as the temperature and length of time the valve is open. Initially, these parameters are adjusted using the trial and error method. The parameters are optimized using an analytical balance to measure the amount of wax dispensed. After the amount is repetitively dispensed within the desired weight range, the parameters are set and used to produce microtubes containing wax.

Figure 4:
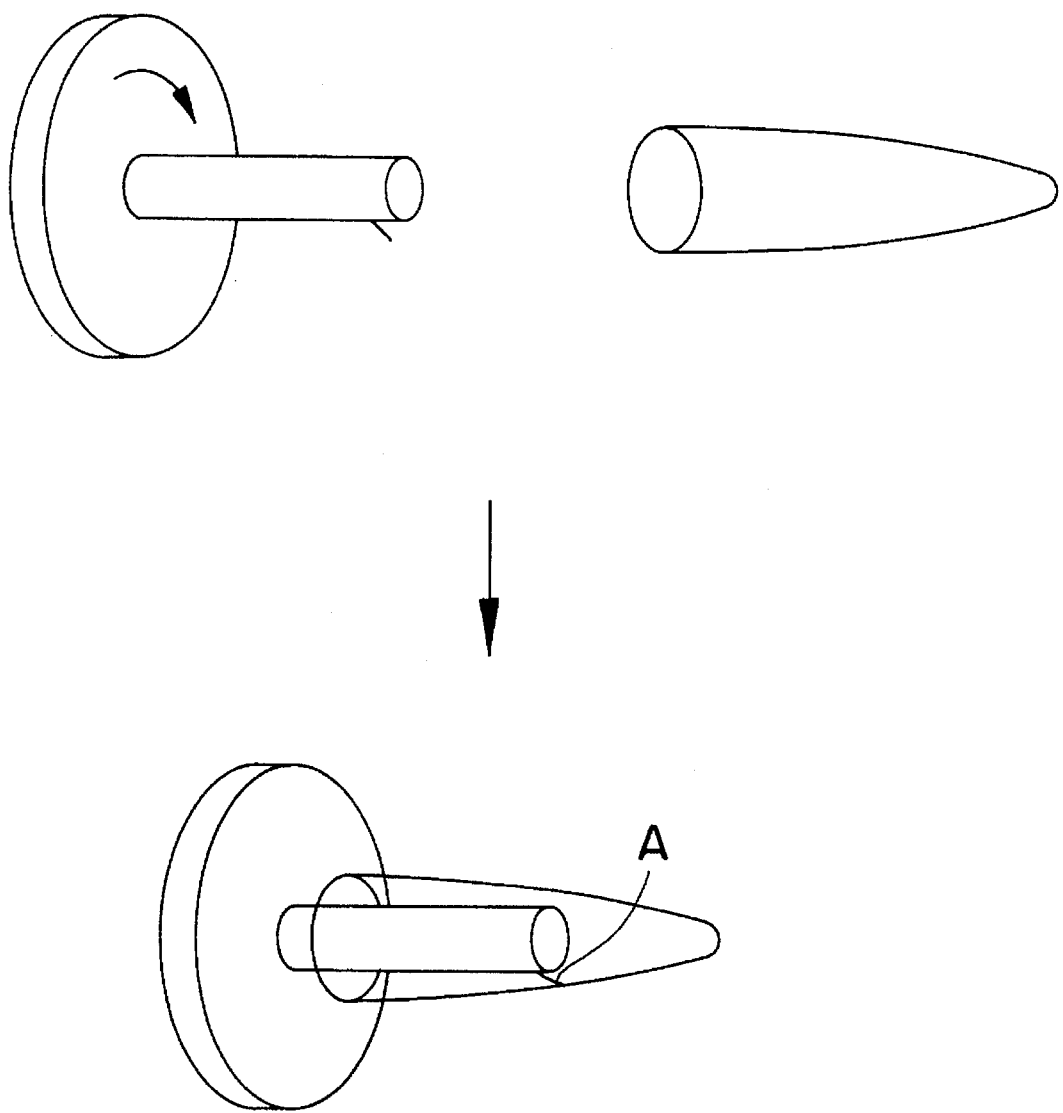
FIG. 4 is a projection diagram of the nozzle with an attached wheel and the PCR container. The wheel is used to adjust the position of the nozzle tip relative to the container. The open end of the PCR container is placed over the nozzle and butts squarely against the side surface of the wheel. The wheel is moved to position the nozzle tip relative to the PCR container. The wheel is attached to the nozzle by a set screw. Structure A is that of FIG. 3.

The wax is positioned on the inside surface of the microtube by means of an adjustable wheel as shown in FIG. 4. A microtube is placed over the nozzle and the open end of the microtube squarely placed against the side of the wheel. The wheel is attached to the nozzle by means of a set screw. The position of the nozzle tip relative to the microtube is adjusted by moving the wheel to position the tip as desired. The position of the wax is assayed by measuring the distance between the wax and closed end of the microtube.

To minimize contamination, microtubes are irradiated an electron beam at an appropriate dose, for example, 2 megarads. Sterilized wax is then deposited in the irradiated microtubes. The microtubes containing wax are stored in sterile containers and assayed for nucleic acid and nuclease contamination.

Although the invention is described with reference to the disclosed embodiments, it should be understood that various modifications can be made without departing from the spirit of the invention. Accordingly, the invention is limited only by the following claims.

We claim:

1. A PCR container consisting of the following elements:
   a) a container that is suitable for PCR; and
   b) has a closed end, an open end distal to the closed end, and a lumen; and
   c) a wax attached to the inside surface of the container wherein:
   d) the wax is at about the meniscus or above the meniscus position of a PCR mixture added to the container;
   e) the wax does not completely occlude the lumen of the container such that the PCR mixture can be added to, the container below the wax without penetrating the wax;
   f) the wax is solid at about 40° C. or below 40° C. and liquid above 40° C.;
   g) the wax, when liquefied, spontaneously covers the surface of the PCR mixture in the container; and
   h) the wax is in an amount that, when liquefied, completely covers the surface of the PCR mixture, with the provision that the inside surface to which the wax is attached is not the bottom of the container and the PCR mixture has not been added to the container.

2. The PCR container of claim 1 wherein the container is a microtube.

3. The PCR container of claim 1 wherein the container is a well in a microtiter plate.

4. The PCR container of claim 1 further comprising the PCR mixture.

5. The PCR container of claim 1 wherein the wax is positioned not less than 0.1 inches from the closed end of the container.

6. The PCR container of claim 5 wherein the container is a conical microtube.

7. The PCR container of claim 5 wherein the amount of wax is about 0.01 to 0.04 g.

8. The PCR container of claim 1 wherein the wax is positioned not more than 0.6 inches from the closed end of the container.

9. A PCR method comprising the following steps:
   a) adding a PCR mixture to the PCR container of claim 1;
   b) thermally cycling the PCR mixture through PCR temperatures; and
   c) completing the PCR method.

10. A hot start PCR method comprising the following steps:
   a) adding a PCR mixture lacking an essential reagent to the PCR container of claim 1;
   b) heating the PCR container of claim 1 to a PCR temperature;
   c) adding the essential reagent lacking in step a to the PCR mixture lacking the essential reagent;
   d) thermally cycling the PCR mixture through the PCR temperatures; and
   e) completing the hot start PCR method.

* * * * *